US00PP07934P

United States Patent [19]

Hanes

[11] Patent Number: Plant 7,934

[45] Date of Patent: Aug. 11, 1992

[54] GERANIUM NAMED AMERICANA CORAL

[75] Inventor: Mitchell Hanes, Morgan Hill, Calif.

[73] Assignee: Goldsmith Seeds, Inc., Gilroy, Calif.

[21] Appl. No.: 656,705

[22] Filed: Feb. 19, 1991

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new Geranium plant particularly distinguished by its coral colored semi-double flowers which are borne on sturdy upright stems. Each flower cluster consists of about 25 to 30 florets, each of which has a diameter of about 4 to 4.5 cm.; the color of the flower changing little with age. The plant itself is vigorous, free flowering and fast-rooting, growing to a height of 13 to 16 cm. as a 5½ inch potted plant.

1 Drawing Sheet

BACKGROUND OF THE NEW PLANT

The present invention comprises a new and distinct cultivar of Geranium, botanically known as *Pelargonium hortorum* Bailey. The new cultivar is propagated from a seedling resulting from the cross of: a seed parent that is scarlet colored with a semi-double flower form that was developed at Goldsmith Seeds and is known as 996-2 and a pollen parent that is an inbred line that is rose colored, single flower known as KR07-3.

This new Geranium is a product of a planned breeding program intended to create new Geranium cultivars with coral colored flowers, semi-double flower form, green foliage, vigorous growth and superior cutting productivity.

The new cultivar was created in 1987 in Gilroy, Calif., and has been repeatedly asexually reproduced by cuttings in Gilroy, Calif., and Guatemala over a three year period. It has also been trialed at Okemos, Mich. It has been found to retain its distinctive characteristics through successive propagations; and this novelty appears to be firmly fixed.

DESCRIPTION OF THE DRAWING

This new Geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

The following detailed descriptions set forth the distinctive characteristics of this new geranium cultivar. The data which defines these characteristics were collected from asexual reproductions carried out in Gilroy, Calif. The plant history was taken on 20 week old plants, blossomed under natural light in a greenhouse. Color readings were taken in the greenhouse on May 29, 1990 at 2P.M. under ambient light. Color references are primarily to The R.H.S. Colour Chart of The Royal Horticultural Society of London (R.H.S.).

THE PLANT

Classification:

*Botanical.*—*Pelargonium hortorum* Bailey.

*Commercial.*—Zonal geranium.

Form: Intermediate height bush.

Height: 13 to 16 cm., as a 5½ inch pot plant, excluding blooms.

Growth: Vigorous, well branched.

Strength: Free flowering plant that does well in greenhouse and outdoor field culture. Good shipping ability as rooted or unrooted cuttings.

Foliage: Abundant quantity.

Leaves:

*Size.*—Diameter about 6–8 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 4 to 5 cm. long.

*Color.*—Upper side: Green. Underside: Lighter green color. Ribs and veins not prominently different from upper surface.

Petioles: About 4 to 7 cm. in length.

THE BUD

Size:

*Diameter.*—About 6 mm.

*Length.*—About 1.4 cm. to 1.9 cm. at time of bud opening.

Shape: Pointed ovoid.

Color: Of petals when sepals first divided, RHS 57-B.

Sepals: Five in number, flat behind petals, Pointed linear lanceolate, RHS 143-C in an open flower.

THE FLOWER

Blooming habit: Continuous throughout the year.

Size: Approximately 4–4.5 cm. diameter, 1.0 cm. deep, irregularly radially symmetrical.

Form: Irregularly shaped when bloom first opens, later flattening with maturity.

Petals: Five to nine imbricate outer petals (mostly five), 1.5–2.0 cm. wide and approximately 2.1–2.3 cm. long, Four to six inner smaller petaloids of varying shape. Both the outer petals and inner petaloids are coral, RHS 43-B. Veins not significantly different from the interveinal regions. Color changing little with age. Underside of petals much lighter in color and exhibiting white striations and white patches. Petals and petaloids soft and satiny.

Pedicel: Approximately 2.3 cm. in length.

Persistence: Nonshattering flower.

INFLORESCENSE

Type: An umbel composed of approximately 25–30 flowers, erect or laterally ascending.

Peduncle: Approximately 10.5–12 cm. in length; color: green RHS 143C.

REPRODUCTIVE ORGANS

Stamens:

*Anthers.*—Six to eight positioned below the mature stigma, dull red prior to anthesis.

*Filaments.*—White near base and mid length, graduating to a red stripe on the outer edges starting at the center of the filaments extending to the anther.

*Pollen.*—Orange in color.

Pistil:

*Number.*—One.

*Length.*—Approximately 7 mm.

Stigma: Five (sometimes six) linear lobes of near equal length, curling back toward ovary, purplish-red.

Style:

*Length.*—About 3mm., color: purplish red.

Ovaries: At anthesis, densely pubescent with white hairs, oblong, Green drying to a light brown at maturity.

Fruit: Partially fertile.

I claim:

1. A new and distinct Geranium cultivar substantially as herein shown and described characterized by green foliage with coral-colored semi-double flowers on large umbels, the plant being fast-rooting and having a vigorous growth habit.

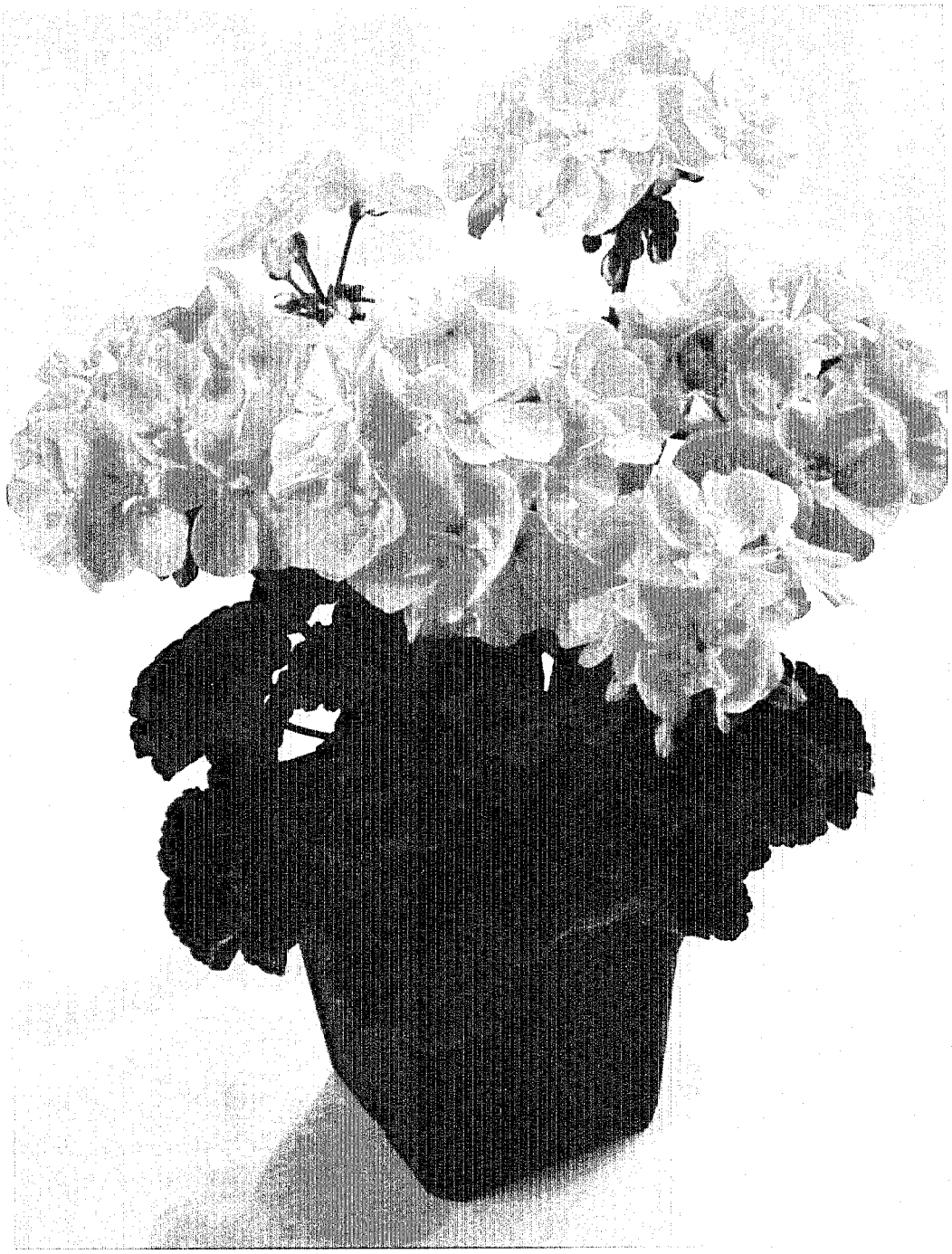

* * * * *